United States Patent

Matsumura

[11] 4,098,549
[45] Jul. 4, 1978

[54] EYE BOTTOM CAMERA
[75] Inventor: Isao Matsumura, Yokohama, Japan
[73] Assignee: Canon Kabushiki Kaisha, Tokyo, Japan
[21] Appl. No.: 658,874
[22] Filed: Feb. 18, 1976
[30] Foreign Application Priority Data
Feb. 24, 1975 [JP] Japan .................. 50-22601
[51] Int. Cl.² .............. A61B 3/14; G03B 29/00
[52] U.S. Cl. ............................ 351/7; 351/6; 354/62
[58] Field of Search ............ 351/7, 13, 14, 16; 354/62

[56] References Cited
U.S. PATENT DOCUMENTS

| | | |
|---|---|---|
| 3,594,071 | 7/1971 | Okajima .................. 351/7 |
| 3,851,954 | 12/1974 | Kato et al. ............... 351/7 |
| 3,925,793 | 12/1975 | Matsumura et al. ....... 351/7 X |

Primary Examiner—John K. Corbin
Assistant Examiner—John D. Lee
Attorney, Agent, or Firm—Toren, McGeady and Stanger

[57] ABSTRACT

The present invention relates to an eye bottom camera which is so designed that in order to eliminate the undesired light beam reflected by the objective lens opposed to the eye to be inspected the objective lens as one group of biconvex type whereby by making the undesired light beams reflected on both surface of the objective lens as if they were produced by a light beam emitted from a same plane of the illumination optical system the small black spot provided on the same plane can be made small and further by so designing that the image formed in the neighborhood of the objective lens, of the small black spot appears at the position closer to the eye to be inspected than the surface of the objective lens it is made difficult that the small black spot be formed on the eye bottom to be inspected.

3 Claims, 5 Drawing Figures

EYE BOTTOM CAMERA

FIELD OF THE INVENTION

The present invention relates to an eye bottom camera.

DISCLOSURE OF PRIOR ART

In case of an eye bottom camera of such a type in which the illumination optical system and the observation photographic optical system presents a common objective lens facing to the eye to be inspected, a part of the light beam coming from the above mentioned illumination optical system is reflected by the cornea of the eye to be inspected or the surfaces of the objective lens. If this reflected light beam enters into the observation photographic optical system a ghost or a flare is produced, whereby the eye bottom can not be observed nor photographed clearly. Until now the undesired light beam reflected on the surface of the cornea of the eye to be inspected has effectively been eliminated by the ring illumination method. On the other hand, so far as the undesired light beam reflected on the surfaces of the objective lens is concerned, there are such methods that the reflecting mirror for leading the light beam of the illumination optical system to the observation photographic optical system is constructed as concave mirror or that as objective lens a group of meniscus lenses are used whereby in the neighborhood of the optical axis a small black spot for shading the light is provided. However, in the former case the optical axis is declined so that the aberration is increased and the resolving power is decreased, while in the latter case there is a danger that the observation photographic light beam in the neighborhood of the optical axis of the objective lens be shaded and furthermore the photographic angle can not be made more than 30° because the meniscus lenses are used.

In case of an eye bottom camera so designed that a biconvex lens is used as an objective lens facing to the eye to be inspected in order to obtain a wider photographic angle quite recently it is proposed that a black spot is provided in the illumination optical system in such a manner that the undesired illumination light beam reflected by the objective lens and entering into the observation photographic optical system is shaded by the above mentioned black spot. The U.S. Pat. No. 3,594,071 relates to a camera in accordance with this method, whose one embodiment is shown in FIG. 1. In FIG. 1, reference character 1 represents an eye to be inspected, 2 a biconvex objective lens, 3 a light source, 4, 5 and 6 a condenser lens, 7 a reflecting mirror having an aperture or boring at the center, 8 a slit, 9 a photographic lens and 10 a photographic plane. The undesired light beam reflected by the surfaces $S_1$ and $S_2$ of the objective lens 2 is eliminated as follows in accordance with the present method. The dotted line $d_1$ shows an undesired light beam coming from the illumination optical system. It is reflected on the $S_1$ surfaces facing to the eye to be inspected, of the objective lens 2. It reaches the photographic plane 10 through the mirror 7 and slit 8 causes a flare or a ghost. This undesired light beam $(d_1)$ is radiated from a point $A_1$ on the condenser lens 5, passes through the condenser lens 6, and the reflecting mirror 7 and is condensed in the neighborhood of the top of the $S_2$ surface of the objective lens 2. The undesired light beam passes the $S_2$ surface, is reflected on the $S_1$ surface, passes again the $S_2$ surface and condensed at the point $A_2$ on the opening of the slit 8 through the boring of the mirror 7. Namely in case of the camera constructed as mentioned above, out of the image of the slit 8 that by means of the light beam reflected on the $S_1$ surface is formed in the neighborhood of the $S_2$ surface. On the other hand, the undesired light beam reflected on the $S_2$ surface of the objective lens and passing through the opening of the slit 8 is that which is reflected in a small area in the neighborhood of the $S_2$ surface. Thus by making the black spot at the point $A_1$ large, an illumination light beam reaching the range in which the undesired light beam is reflected on the $S_2$ surface is shaded in order to eliminate the undesired light beam reflected on the $S_2$ surface. Thus in case of the conventional eye bottom camera shown in FIG. 1, the position of the small black spot in the illumination system is almost conjugate with that of the top of the $S_2$ surface.

In case of the eye bottom camera so designed that a small black spot is provided in the illumination optical system so as to eliminate the undesired light beam reflected on both surfaces of the biconvex objective lens facing to the eye to be inspected, care must be taken so that an image of the small black spot should not be formed on the eye bottom and cover a part of the eye bottom.

SUMMARY OF THE INVENTION

The purpose of the present invention is to offer an eye bottom camera which is so designed that by means of a small black spot provided in the illumination optical system the undesired light beam reflected on both surfaces of the biconvex objective lens is eliminated, whereby it is made difficult for the black image of the above mentioned small black spot to be formed on the eye bottom to be inspected.

In case of the eye bottom camera in accordance with the present invention, by so designing that the objective lens facing to the eye to be inspected is composed as one group of biconvex type in such a manner that the undesired light beams reflected on both surfaces of the objective lens are made as if radiated from the same plane of the illumination optical system, the small black spot for shading the light, provided in the above mentioned same plane can be made small and further the image of the small black spot is formed at a position closer to the eye to be inspected than the objective lens.

BRIEF DESCRIPTION OF THE DRAWINGS:

FIG. 4(A) shows the conventional eye bottom camera, while FIG. 4(B) shows the eye bottom camera in accordance with the present invention.

DETAILED DESCRIPTION OF PREFERRED EMBODIMENT

Figure 1:
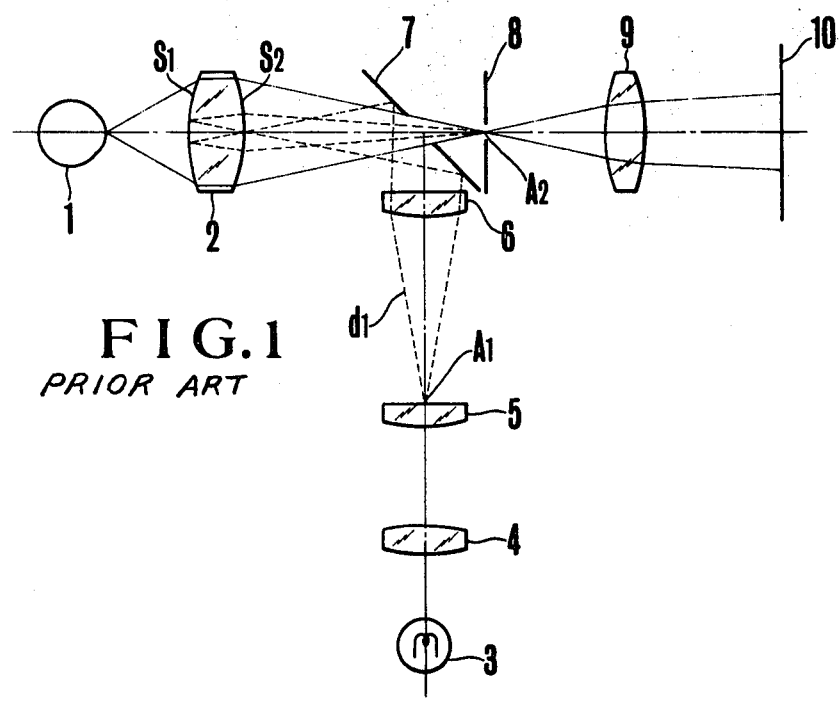
FIG. 1 shows a conventional eye bottom camera.

In order to avoid the apparition of the image of a small black spot on the eye bottom to be inspected, the following two points must be taken into consideration.

The first condition is that the small black spot provided in the illumination optical system must be as small as possible. The second condition is that the position of the image of the small black spot in the neighborhood of the objective lens must be as far as possible from the position at which the image of the eye bottom to be inspected is formed by the objective lens. FIG. 2 is the enlarged sketch of the neighborhood of the objective lens 2 for explaining the above mentioned two conditions, whereby the same elements as in FIG. 1 bear the same figures. In FIG. 2, the dotted line $d_2$ shows the illumination light beam coming from the illumination light source, while the full line $d_3$ shows the light beam to be used for the observation and the photographing out of the light beam reflected from the eye bottom.

At first, the above mentioned first condition will be explained. Generally the F-number of the illumination light beam for illuminating the eye bottom is almost the same as that of the pupil of the person to be inspected so that it is almost constant. In consequence the converging angle $\theta$ of the illumination light beam is almost constant.

In case as is shown in FIG. 2, the converging angle of the illumination light beam is $\theta$ while the black spot in the illumination light beam optical system is formed at $A_3$, for example a screen is placed at $A_3$ so as to be moved along the optical axis 0–0'. When the small black spot is small enough, the range $E_1$ in which the image of the black spot appears around $A_3$ as center is comparatively larger, while the small black spot is large the range $E_2$ becomes comparatively small. When the image of the eye bottom of the person with normal visibility is formed at $A_4$ by the objective lens, the image of the eye bottom of the person with short sightedness is formed at the point closer to the eye to be inspected than the point $A_4$. This point $A_4$ is optically conjugate with the eye bottom to be inspected with regard to the objective lens 2, so that when the point $A_4$ is supposed to be at the eye bottom to be inspected the image of the small black spot is actually formed on the eye bottom to be inspected in case the point $A_4$ is in the above mentioned ranges $E_1$ and $E_2$. The sharper the image of this small black spot is, the closer the point $A_4$ is to the point $A_3$. Thus the larger the ranges ($E_1$, $E_2$) are, namely the larger the small black spot is, more likely the image of the small black spot is formed on the eye bottom to be inspected.

The second condition means that the image forming position $A_3$ of the above mentioned black spot is distant from the above mentioned point $A_4$, because the sight of men assumes almost normal distribution around those whose sight is standard as center. Therefore, in case the point $A_3$ is sufficiently distant from the point $A_4$, the small black spot is never formed on the eye bottom unless the person to be inspected possesses extremely abnormal sight.

In accordance with the present invention in order to meet the first condition it is so designed that the undesired light beams reflected from both surfaces of the objective lens and misted into the photographic optical system be radiated from the same surface of the illumination optical system, while in order to meet the second condition the eye bottom camera is so designed that the image of the black spot provided in the above mentioned illumination system be formed closer to the eye to be inspected than the face $S_2$ of the objective lens.

Figure 3:
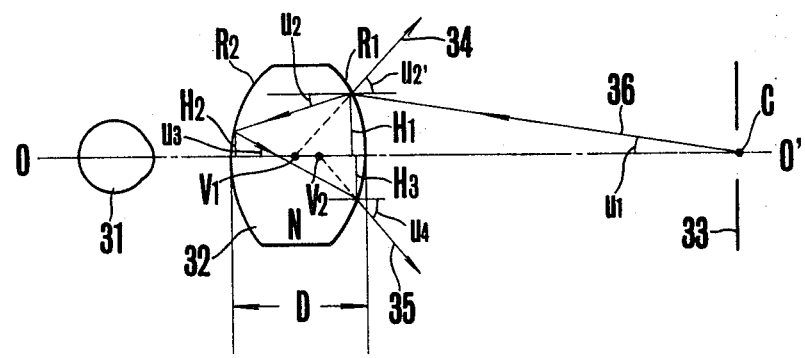

FIG. 3 is the sketch for explaining the method to meet the above mentioned first condition. In FIG. 3, 31 is the eye to be inspected while 32 is a biconvex objective lens whereby the radius of curvature of the surface opposed to the eye to be inspected is $r_2$ (hereinafter this surface is called $R_2$ surface), that of the other surface is $r_1$ (hereinafter this surface is called $R_1$ surface), the thickness D and the index of refraction N. 33 is the diaphragm plate intended to limit the light beam entering into the photographic optical system. Hereby 0–0' is the optical axis.

The above mentioned first condition means that the position $V_1$ of the imaginary image formed by the light beam reflected by the $R_1$ surface of the diaphragm plate 33 for limiting the light beam entering into the photographic optical system coincides with that $V_2$ of the imaginary image of the diaphragm plate 33 formed by the light beam 35 coming from the diaphragm plate 33, entering through the $R_1$ surface, reflected by the $R_2$ surface and again going out through the $R_1$ surface. Namely the $R_1$ surface and the $R_2$ surface are designed in such a manner that the position $V_1$ coincides with the position $V_2$.

Now let us consider about the light beam reflected on the $R_1$ surface. Let the angle between the light beam 36 radiated from the center of the diaphragm plate 33 and directed to $H_1$ on the $R_1$ surface and the optical axis (0–0') be $U_1$ and the angle of the light beam 34 reflected on the $R_1$ surface and the optical axis (0–0') be $U'_2$, so the following relation is established.

$$U'_2 = U_1 - (2/r_1)H_1 \tag{1}$$

Hereby the index of refraction of the air is taken as 1.

On the other hand with reference to the light beam reflected on the $R_2$ surface, the following relations are established.

$$NU_2 = U_1 + \frac{N-1}{r_1} H_1 \tag{2}$$

$$H_2 = H_1 - \frac{D}{N} \cdot NU_2 \tag{3}$$

$$NU_3 = NU_2 - \frac{2N}{r_2} H_2 \tag{4}$$

$$H_3 = H_2 - \frac{D}{N} NU_3 \tag{5}$$

$$U_4 = NU_3 + \frac{N-1}{r_1} H_3 \tag{6}$$

whereby $U_1$ is the angle between the light beam 36 radiated from the center C of the diaphragm plate and directed to $H_1$ of the $R_1$ surface and the optical axis (0–0'), $U_2$ the angle between the light beam refracted on the $R_1$ surface and directed to the $R_2$ surface and the optical axis (0–0'), $U_3$ the angle between the light beam reflected on the $R_2$ surface and directed to the $R_1$ surface and the optical axis (0–0') and $U_4$ the angle between the light beam going out again from the $R_1$ surface and the optical axis (0–0').

From the above mentioned equations (1) to (6), the position $V_1$ of the imaginary image of the point C by means of the light beam reflected by the $R_1$ surface and directed to the diaphragm plate is represented as follows with reference to the $R_1$ surface, $$(H_1/U'_2)$$

On the other hand, the position $V_2$ of the point C by means of the light beam refracted on the $R_1$ surface, reflected on the R₂ surface and going out again from the R₁ surface, $(H_3/U_4)$ The combination of the parameters $U_1, r_1, r_2, D$ and $N$ of the above mentioned objective lens is chosen in such a manner $(H_1/U_2)$ is equal or almost equal to $(H_3/U_4)$, when the position $V_1$ coincides with the position $V_2$. Hereby the undesired reflected light beam can be eliminated only if the small black spot is provided at a point in the illumination optical system which is a conjugate point with that at which the position $V_1$ coincides with the position $V_2$.

Figure 2:
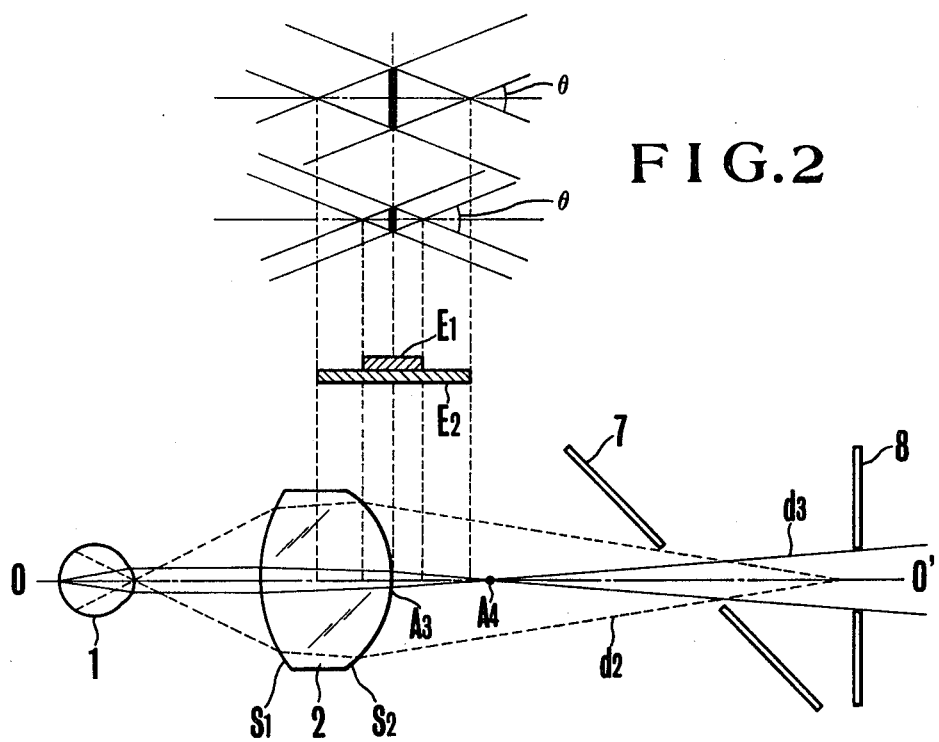
FIGS. 2 and 3 respectively show a sketch for explaining the eye bottom camera in accordance with the present invention.
Figure 4:
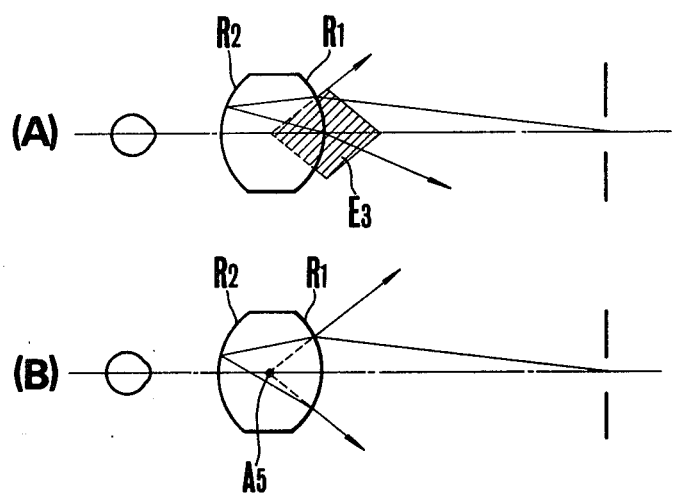
FIG. 4(A) and FIG. 4(B) show sketches for comparing the effects of the eye bottom camera in accordance with the present invention with that of the conventional eye bottom camera, whereby

Consequently in accordance with the method shown in FIG. 1, the reflection on the $R_1$ surface is covered by the black point with dimension necessary on the $R_1$ surface so that, as is shown in FIG. 4, the range $E_3$ is shaded. Namely between the $R_1$ surface and the position of the imaginary image by the light beam reflected on the $R_1$ surface a black spot appears in a wide range before and behind the $R_1$ surface whereby further the black spot is large. On the other hand in case of the optical system in accordance with the present invention, as is shown in FIG. 4(B), the reflections at the $R_1$ surface and the $R_2$ surface can be eliminated at the one point $A_5$ so that the position at which the black spot appears is only one and further the black spot may be small. In the above mentioned explanation only the light beam from the center C of the diaphragm plate is taken in consideration, while the actual diaphragm plate presents a certain area so that the black spot also presents a certain area and therefore the range in which the black spot appears at the eye bottom becomes larger.

With reference to the second condition as is clear in case of the present invention, it is so designed that the image of the small shading black spot for eliminating the undesired reflection light bema is formed at the position closer to the eye to be inspected than the above mentioned $R_1$ surface so that the image of the black spot is hard to be formed at the eye bottom.

Figure 5:
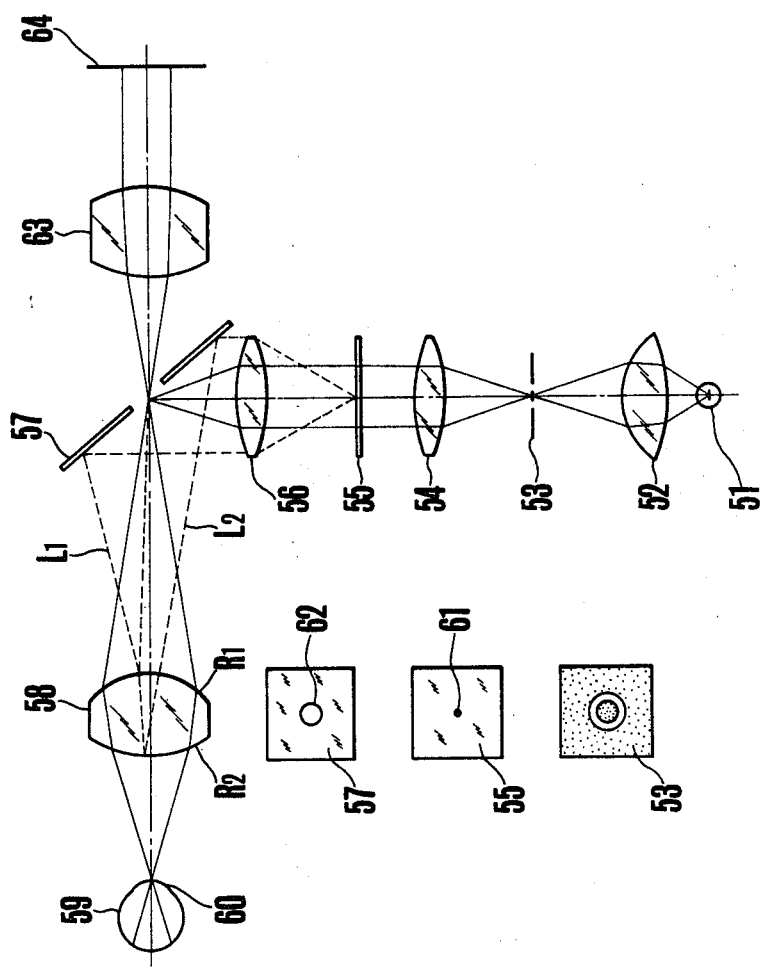
FIG. 5 shows an embodiment of the eye bottom camera in accordance with the present invention.

FIG. 5 shows an embodiment in accordance with the present invention. In FIG. 5, 51 is the light source, 52 the condenser lens, 53 the ring slit; 54, 56 the relay lenses and 55 the glass plate presenting a small shading black spot 61 in the neighborhood of the optical axis. 57 is an apertured inclined mirror, for example, a mirror presenting a boring 62 at the center. 58 is a biconvex objective lens, 59 the eye to be inspected, 60 the cornea, 63 the relay lens and 64 the photographic plane.

The light beam radiated from the light source 51 is condensed at the ring slit 53 by means of the condenser lens 52. The ring shaped light beam coming from the opening of the ring slit 53 is condensed again on the cornea of the eye to be inspected, by means of the relay lenses (54, 56), the mirror 57 with a boring and the objective lens 58 so as to illuminate the eye bottom. In order to eliminate the undesired light beams $(L_1, L_2)$ reflected on the $R_1$ surface and the $R_2$ surface of the objective lens 58 a plane glass is provided between the relay lenses 56 and 54. On the plane glass a small black spot for shading the light whereby the small black spot 61 is provided on the optical axis of the illumination optical system. As explained above, the small black spot 61 for shading the light on the plane glass plate 55 is determined in such a manner that among the light beam from the light source 51, passing through the small black spot 61 and directed to the objective lens 58 by means of the mirror 57 with boring, the images of both the light beam $L_1$ reflected on the $R_1$ surface of the objective lens and the light beam $L_2$ passing through the $R_1$ surface, reflected on the $R_2$ surface and again passing through the $R_1$ surface are formed at the opening of the mirror 57 with opening. In other words, in case of the light beam directed from the opening 62 of the mirror with a boring to the eye to be inspected, the light beam $L_1$ reflected on the $R_1$ surface is condensed on the above mentioned small black spot by means of the mirror 57 with boring and the relay lens 56, while the light beam $L_2$ passing the $R_1$ surface, reflected on the $R_2$ surface and again passing the $R_1$ surface is condensed on the above mentioned small black spot 61 by means of the mirror 57 with a boring and the relay lens 56.

In the foregoing description, for better understanding of the present invention, the black spot and the inclined mirror's aperture have been explained as if rays of light emanate therefrom. However, this is no more than a convenient means of explaining the features of the present invention. In practice, the black spot functions to shield some fraction of the light beam from the light source, and therefore no light emanates from the black spot. Further, the light beam emanating from the aperture of the inclined mirror is shown as a means for better understanding the effects of the invention, and such emanation of the light beam from the aperture also does not occur in practice. Therefore, with respect to the optical systems including respective surfaces R1 and R2 of the objective lens as the reflection surfaces, as is also evident from the description made by use of the above mentioned light rays, there are arranged the black spot and the inclined mirror's aperture in optically conjugate positions to each other, so that as a matter of course the undesired reflecting light rays produced from the $R_1$ and $R_2$ surfaces of the objective lens do not pass through the aperture of the inclined mirror.

Below serve concrete embodiments of the shapes of the objective lens for eliminating the undesired reflected light beam are given.

(Embodiment 1)

$r_1$ = non-spherical surface basing upon −31.674
$r_2$ = 53.769
$D$ = 39.2      $n$ = 1.568         $S_1$ = 114.1
$f$ = 42.06    $|m^1|$ = 0.12    $|m^2|$ = 0.2

(Embodiment 2)

$r_1$ = −51.146
$r_2$ = non-spherical surface basing upon 35.525
$D$ = 43.85    $n$ = 1.568         $S_1$ = 114.1
$f$ = 45.02    $|m^1|$ = 0.18    $|m^2|$ = 0.13

Hereby;
$r_1$ : radius of curvature of the surface at the side of the mirror with boring
$r_2$ : radius of curvature of the surface at the side of the eye to be inspected
$D$ : Thickness of lens
$n$ : Index of lens
$S_1$ : Distance between the mirror with boring and the $r_2$ surface
$f$ : Focal distance of the objective lens
$m^1$ : Magnification factor of the imaginary image of the light beam from the small black spot reflected on the $R_1$ surface
$m^2$ : Magnification factor of the imaginary image of the light beam from the small black spot reflected on the $R_2$ surface.

Hereby in case of the embodiment either of the $R_1$ surface and $R_2$ surface is made non-spherical in order to eliminate the light reflected on the cornea, whereby the non-spherical surfaces can be exchanged for each other or both surfaces can be made spherical.

Further when in case of the present optical system, the radius of curvatures of $r_2$ surface and $r_1$ surface are made equal to each other and the thickness D of the lens is also made equal to this radius of curvature, the magnification factors of the imaginary image can also be made equal to each other as follows in such a manner that the small black spot for shading light can be minimized $$|m1| = |m2|$$

What is claimed is:

1. An opthalmoscopic camera comprising:
a photographic system defining an optical path; said system including biconvex objective lens means along the optical path, a photographic lens along the optical path, a mirror along the optical path between said lens and said lens means, said mirror having a central aperture and being inclined relative to said path, said biconvex objective lens means having a first surface $R_1$ facing the mirror and a second surface $R_2$ away from the mirror;

an illumination system forming an illuminating light path; said system including a light source, a condenser lens and relay lens means in succession along the illuminating path and directing light at said mirror, said mirror being inclined for deflecting light from said illuminating system along the optical path and through the objective lens means so that the light can be directed onto the cornea of an eye to be inspected, light from positions in the illumination system being reflected by the mirror through the objective lens means where part of the light may be reflected by the first surface $R_1$ of the biconvex objective lens means and part of the light is reflected by the second surface $R_2$ of the biconvex objective lens means, said illumination system having a transparent plate with a black spot, the aperture of said mirror and the black spot on said transparent plate being optically conjugate with respect to a first path that includes said mirror and said transparent plate as well as said surface $R_1$ as a reflection surface and a second path that includes said mirror and said transparent plate as well as the surface $R_2$ as a reflection surface.

2. A camera in accordance with claim 1, wherein said relay means includes first and second relay lenses along the illuminating paths and wherein the transparent plate including the black spot is located between the first relay lens and the second relay lens.

3. A camera in accordance with claim 2, wherein $m_1 = m_2$, whereby $m_1$ is the magnification factor of the imaginary image of the small black spot by means of the light beam coming from the small black spot reflected on the surface $R_1$, while $m_2$ is the magnification factor of the imaginary image of the small black spot by means of the light beam passing the surface $R_1$, reflected on the surface $R_2$ and refracted at the surface $R_1$.

* * * * *